United States Patent
Winn

[11] 4,180,669
[45] Dec. 25, 1979

[54] 2-(N-PHENETHYL-4-PIPERIDINO)-5-PENTYL RESORCINOL

[75] Inventor: Martin Winn, Deerfield, Ill.

[73] Assignee: Abbott Laboratories, North Chicago, Ill.

[21] Appl. No.: 890,154

[22] Filed: Mar. 27, 1978

Related U.S. Application Data

[63] Continuation-in-part of Ser. No. 749,634, Dec. 13, 1976, abandoned.

[51] Int. Cl.$^2$ ............................................. C07D 211/22
[52] U.S. Cl. ................................... 546/240; 424/267; 546/124; 546/344
[58] Field of Search .......... 260/297 R, 297 B, 293.83, 260/293.84, 293.54; 546/240

[56]  References Cited
U.S. PATENT DOCUMENTS 3,951,970   4/1976   Razdan et al. .................. 260/293.84

FOREIGN PATENT DOCUMENTS 1220201  1/1971  United Kingdom ................ 260/297 R

OTHER PUBLICATIONS

Chemical Abstracts, 49:318a (1955) [Sommers, A., et al. J. Am. Chem. Soc., 75, 5280–5283 (1953).]
Chemical Abstracts, 31:16327 (1937),[German Pat. No. 639,125, 12/16/36.]

Primary Examiner—John M. Ford
Assistant Examiner—Richard A. Schwartz
Attorney, Agent, or Firm—Paul D. Burgauer; Robert L. Niblack

[57] ABSTRACT

This invention provides 2-(N-substituted piperidino)-5-alkyl resorcinols of the structure

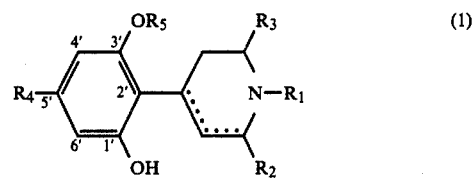

wherein $R_1$ is H, loweralkyl, loweralkynyl or aralkyl; $R_2$ and $R_3$ are each H or when taken together $R_2R_3=CH_2CH_2$; $R_4$ is a $C_1$–$C_{10}$ alkyl and $R_5$ is H or loweralkyl, and the pharmaceutically acceptable salts thereof.

These compounds are useful as antisecretory agents.

1 Claim, No Drawings

2-(N-PHENETHYL-4-PIPERIDINO)-5-PENTYL RESORCINOL

BACKGROUND OF THE INVENTION

This is a continuation-in-part of our previously filed application Ser. No. 749,634 filed Dec. 13, 1976, now abandoned.

In past studies, analogs of tetrahydrocannabinol have been found to exhibit antisecretory activity. However, these compounds in addition to their antisecretory activity, exhibited analgesic, sedative and antihypertensive activity. In attempting to provide compounds having antisecretory activity but not analgesic or antihypertensive activity, a series related to tetrahydrocannabinols, which lacked the pyran ring, were prepared.

By the present invention, it has been found that several piperidino resorcinols exhibit strong antisecretory activity without analgesic, sedative or antihypertensive activity.

SUMMARY OF THE INVENTION

The present invention provides compositions which exhibit antisecretory activity and include as the active ingredient, a 2-(N-substituted piperidino)-5-alkyl resorcinol of the structure:

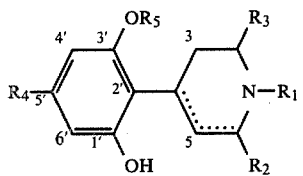

wherein $R_1$ is H, loweralkyl, loweralkynyl or arylloweralkyl; and $R_2$ and $R_3$ are each H or when taken together $R_2R_3$=$CH_2CH_2$; $R_4$ is a $C_1$-$C_{10}$ alkyl; $R_5$ is H or loweralkyl; and the dotted line indicates an optional double bond in the 4–5 or the 5–6 position, and the pharmaceutically acceptable salts thereof.

DETAILED DESCRIPTION OF THE INVENTION

This invention relates to piperidino resorcinols and more particularly to 2-(N-substituted piperidino)-5-alkyl resorcinols. The compounds of the present invention are represented above by formula I. These compounds are useful as antisecretory agents.

As used herein, the term "loweralkyl" refers to $C_1$-$C_6$ straight or branched chain alkyl groups including methyl, ethyl, n-propyl, iso-propyl, n-butyl, sec-butyl, tert-butyl, n-pentyl, iso-pentyl, neo-pentyl, n-hexyl and the like.

The term "loweralkynyl", as used herein, refers to $C_2$-$C_6$ alkyl groups from which two hydrogen atoms have been removed from each of two adjacent carbon atoms to produce acetylenic unsaturation, e.g., ethynyl, propargyl, 2-butynyl, 1-pentyl and the like.

The term "$C_1$-$C_{10}$ alkyl" refers to straight and branched chain alkyl radicals having from 1 to 10 carbon atoms such as methy, pentyl, hexyl, n-heptyl and the like.

As used herein, the term "arylloweralkyl" refers to an alkyl group of 1 to 6 carbon atoms where one of the hydrogen atoms of the alkyl group is substituted by a phenyl group.

The compounds of this invention exhibit oral antisecretory activity at dosages from 1.0 to 30.0 mg/kg of body weight.

The compounds of the present invention may be prepared by means of a variety of methods. For example, the 2-(substituted piperidino)-5-alkyl resorcinols can generally be prepared by reacting either a 5-substituted resorcinol or a 3-methoxy-5-substituted phenol (2) with (a 2,6-substituted) N-substituted-4-piperidone (3) to provide a 2-(N-substituted-1,2,3,6-tetrahydro-4-pyridyl)-5-alkyl resorcinol (4) as illustrated below wherein the substituents have the previously defined meanings, except that $R_1$ is not benzyl or H:

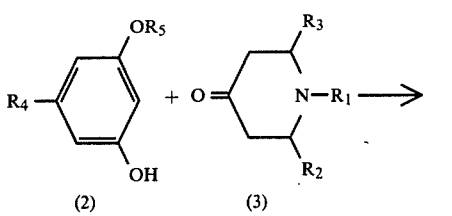

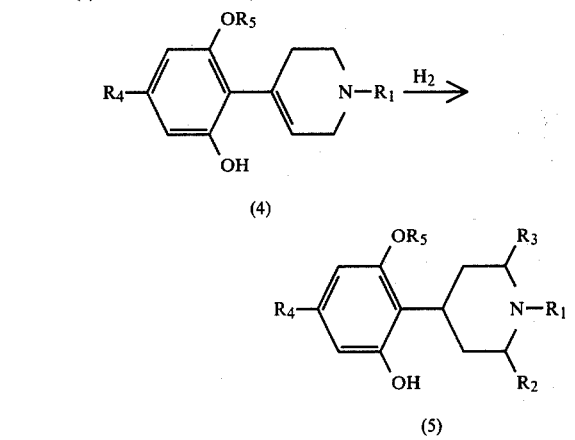

In a similar manner, a 2-(N-benzyl-1,2,3,6-tetrahydro-4-pyridyl)-5-alkyloxy phenol (5) may be prepared by reacting a 5-substituted resorcinol (2) with a N-benzyl-4-piperidone which in turn can be hydrogenated to produce the compound with $R_1$=H (6) as illustrated in the following diagram below:

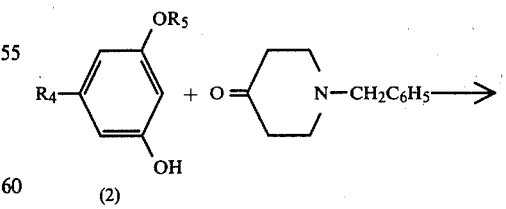

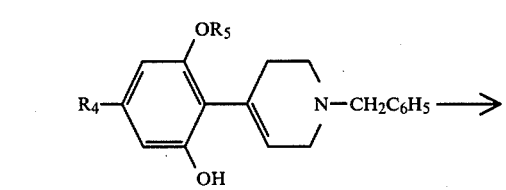

-continued

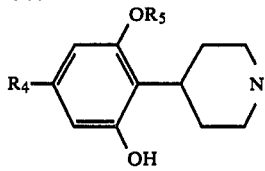

The following examples further illustrate the compounds of this invention. Among the materials used, olivetol was commercially available, the 5-(1,2-dimethylheptyl) resorcinol was prepared according to the method described by Adams et al., *J. Am. Chemical Soc.*, 70, 664 (1948) and 1-isopropyl-4-piperidone was prepared according to the method described in Ziering et al., *J. Org. Chem.*, 12, 894 (1947). All temperatures given are in °C. and in all instances, chemical analyses and/or the nmr spectra were in excellent agreement with the assigned structures.

EXAMPLE 1

5-Isopropyl Resorcinol

Methyl 3,5-dimethoxy benzoate was prepared from the acid by the method described by Clinton and Laskowski, *J. Am. Chemical, Soc.*, 70, 3135 (1948). This ester (196 g, 1 mol.) in 250 ml ether was added to the Grignard reagent prepared from 369 g. methyl iodide and 61 g. magnesium in 1 liter ether, and the reaction mixture was worked up in the usual manner to give 195.3 g. (99%) α,α-dimethyl-3,5-dimethoxybenzyl alcohol, m.p. 50°–52°.

This alcohol (165 g., 0.85 mol.) in 1 l. acetic acid containing 2.5 ml. concentrated $H_2SO_4$ was hydrogenated using 20 g. of 5% Pd/C as a catalyst. After uptake of hydrogen was complete, the catalyst was filtered, the sulfuric acid was neutralized with 6 g. NaOAc and the solvent concentrated in vacuo. Ice was added. The mixture was made basic with KOH solution and extracted with ether. Distillation gave 118.5 g., b.p. 120–125/v mm $n^{25}=1.5082$, 79% yield.

The above dimethyl ether (64.5 g., 0.36 mol.) was refluxed with 800 ml., 48% HBr for 16 hours. The reaction mixture was extracted with ether and the product crystallized from benzene to give 42.0 g., m.p. 110°–113°.

EXAMPLE II 3,5-Dimethoxy Isobutyrophenone

A solution of 1.0 mole isopropyl magnesium chloride in 250 ml. ether was added to a solution of 110 g. (0.675 mol) 3,5-dimethoxybenzonitrile in 350 ml. benzene and 100 ml. ether. After refluxing overnight, the reaction mixture was worked up with dilute HCl giving 127.5 g. product (91%) b.p. 122°–123°/1.5 nm, $n^{25}=1.5265$.

EXAMPLE III 2-(3,5-Dimethoxyphenyl)-3-methylbutane 3,5-Dimethoxy isobutyrophenone (62 g., 0.3 mol.) in 150 ml. ether was added dropwise to 0.4 mol $CH_3MgBr$ in 130 ml. ether, and refluxed 3 hours. The reaction mixture was worked up with $NH_4Cl$ in water giving 67 g. of the intermediate alcohol. This was hydrogenated in 200 ml. acetic acid with 2 ml. $H_2SO_4$ using 10 g. 5% Pd/C as a catalyst. The reaction was worked up as in the preparation of the isopropyl analog to give 57 g. (92%) of product, b.p. 92°–94°/9.7 mm, $n^{25}=1.5055$.

EXAMPLE IV 5-(1,2-Dimethylpropyl)resorcinol

The dimethyl ether (27.0 g., 0.13 mol.), of Example III, in 180 ml. acetic acid and 72 ml. 48% HBr was gassed with 27 g. HBr and the resulting solution heated at 85° for 15 hours and then concentrated in vacuo. Water was added and KOH solution added until the pH was 6.4. Potassium carbonate was added until the pH was 8.4. The mixture was extracted with ether and the product distilled to give 22 g. (93%) viscous oil, b.p. 137°–138°/0.1 mm.

EXAMPLE V 5-(1,2-Dimethylheptyl)-3-methoxyphenol

To 750 ml. cold dimethyl formaldehyde (DMF) was added 100 g. (1.06 mol.) ethanethiol. To this was added slowly 48 g. (1.14 mol.) of 57% NaH in mineral oil (which had been freed of mineral oil by washing with benzene). Then 90 g. (0.34 mol.) 1,3-dimethoxy-5(1,2-dimethylheptyl) benzene was added under a nitrogen atmosphere. The reaction mixture was refluxed overnight. Ice and water (4 l.) was added and the mixture was extracted with ether. The ether extracts were washed twice with 100 ml. 10% $H_2SO_4$, twice with water, dried ($Na_2SO_4$) and distilled. The product had b.p. 134/0.15 mm $n^{25}=1.5090$. Yield 71.5 g. (86%).

EXAMPLE VI 2-(N-Methyl-1,2,3,6-tetrahydro-4-pyridyl)-5-isopropyl resorcinol hydrochloride 5-Isopropyl resorcinol (22.4 g.) and 16.5 g. N-methyl piperidone-4 were dissolved in 45 mm acetic acid. Hydrogen chloride gas was bubbled through for 15 minutes and the solution let stand at room temperature for 3 hours. Excess HCl gas was removed on a rotary evaporator and the solution was treated with isopropyl alcohol to give a crystalline solid, 27.1 g (65% yield); m.p. 273°–275°.

EXAMPLE VII 2-(N-Methyl-1,2,3,6-tetrahydro-4-pyridyl)-5-(1,2-dimethylpropyl) resorcinol hydrochloride 5-(1,2-Dimethylpropyl) resorcinol (15.7 g) and N-methyl-4-piperidone (9.8 g) were dissolved in 35 ml acetic acid and treated with HCl gas as described in Example VI giving 18.8 g of product, m.p. 241°–243°.

EXAMPLE VIII 2-(N-Methyl-1,2,3,6-tetrahydro-4-pyridyl)-5-pentyl resorcinol hydrochloride Olivetol (22.3 g) and N-methyl-4-piperidone (14 g) were dissolved in 50 ml acetic acid and treated with HCl gas as described in Example VI giving 30.6 g (79%) product, m.p. 179°–180°.

EXAMPLE IX 2-(N-Methyl-1,2,3,4-tetrahydro-4-pyridyl)-5-(methyl) resorcinol

Orcinol hydrate (15 g) and N-methylpiperidone (11.0 g) were dissolved in 30 ml acetic acid and treated with HCl gas as described in Example VI giving 6.42 g of product, m.p. 241°–243°.

EXAMPLE X 2-(N-Methyl-1,2,3,6-tetrahydro-4-pyridyl)-5-(1,2-dimethylheptyl) resorcinol 1,2-Dimethylheptyl resorcinol (15.4 g) and N-methylpiperidone (9.9 g) in 32 ml acetic acid gave 12.53 g of product, m.p. 220°–221°.

EXAMPLE XI 2-(N-Benzyl-1,2,3,6-tetrahydro-4-pyridyl)-5-isopropyl resorcinol hydrochloride 5-Isopropyl resorcinol (20.2 g), N-benzyl-4-piperidone (24.6 g) and 45 ml acetic acid was treated with HCl gas as described in Example VI to give 39.15 g product, m.p. 286°–288°.

EXAMPLE XII 2-(1,2,3,6-Tetrahydro-4-pyridyl)-5-isopropyl resorcinol hydrochloride The product of Example XI (30.1 g) was suspended in 150 ml methanol and hydrogenated using 4 g of 5% Pd on carbon. After uptake of 1 mole hydrogen, the catalyst was filtered, the solution concentrated and the residue crystallized from isopropyl alcohol to give 12.27 g (52.5%) of product, m.p. 269°–271°.

EXAMPLE XIII 2-(N-Isopropyl-1,2,3,6-tetrahydro-4-pyridyl)-5-isopropyl resorcinol hydrochloride 5-Isopropyl resorcinol (5.40 g), N-isopropyl-4-piperidone (5.00 g) and 12 ml acetic acid was treated with HCl as described in Example I to give 5.48 g product (50% yield); m.p. 247°–248°.

EXAMPLE IV 2-(N-Benzyl-1,2,3,6-tetrahydro-4-pyridyl)-5-(1,2-dimethylheptyl) resorcinol hydrochloride 1,2-Dimethylheptyl resorcinol (14.7 g) N-benzyl-4-piperidone (11.9 g) and 30 ml acetic acid were treated with HCl gas as described in Example I to give 25.4 g product, m.p. 278°–280° (92% yield).

EXAMPLE XV 2-(1,2,3,6-Tetrahydro-4-pyridyl)-5-(1,2-dimethylheptyl) resorcinol hydrochloride The product of Example XIV (8.97 g) was suspended in 2-methoxy ethanol and hydrogenated using 5% Pd on carbon as a catalyst. After an equivalent of hydrogen was taken up, the catalyst was filtered, the solution was concentrated and the residue crystallized from isopropyl alcohol and ether. Yield 4.50 g, m.p. 235°–238°.

EXAMPLE XVI 2-(4-Piperidino)-5-(1,2-dimethylheptyl) resorcinol hydrochloride

The product of Example XIV (8.86 g) in 2-methoxyethanol was hydrogenated for 38 hours using 3.7 g of 5% Pd on carbon as the catalyst. Yield 5.5 g of product, m.p. 215°–220°.

EXAMPLE XVII 2-(N-Methyl-4-piperidino)-5-(1,2-dimethylheptyl) resorcinol hydrochloride The product of Example X (4.7 g) was hydrogenated in methanol as described in Example XVI to give 4.3 g of product, m.p. 248°–250°.

EXAMPLE XVIII 2-(N-Methyl-4-piperidino)-5-pentyl resorcinol hydrochloride

The product of Example VIII (8.55 g) was hydrogenated in ethanol using 2.2 g 5% Pd on carbon as the catalyst, yield of product 7.28 g, m.p. 155°–158° (isopropyl alcoholether).

EXAMPLE XIX 2-(N-Phenethyl-1,2,3,6-tetrahydro-4-pyridyl)-5-pentyl resorcinol hydrochloride This compound was prepared from 9.0 g olivetol and 10.2 g N-phenethyl-4-piperidone as described in Example VI to give 14.1 g product, m.p. 278°–280°.

EXAMPLE XX 2-(N-Phenethyl-1,2,3,6-tetrahydro-4-pyridyl)-5-(1,2-dimethylheptyl) resorcinol hydrochloride This compound was prepared from 11.8 g 5-(1,2-dimethylheptyl) resorcinol and 10.2 g N-phenethyl piperidone as described in Example VI to give 22.3 g of product, m.p. 284°–286°.

EXAMPLE XXI 2-(N-Phenethyl-4-piperidino)-5-pentyl resorcinol hydrochloride

The product of Example XIX (7.0 g) in 2-methoxy ethanol was hydrogenated as described in Example XI to give 6.6 g of product, m.p. 307°–309°.

EXAMPLE XXII 2-(N-phenethyl-4-piperidino)-5-(1,2-dimethylheptyl) resorcinol hydrochloride The product of Example XX (10.0 g) in 2-methoxy ethanol was hydrogenated as described in Example XV to give 9.6 g product, m.p. 289°–291°.

EXAMPLE XXIII 2-(N-Methyl-2,6-ethylidene-1,2,3,6-tetrahydro-4-pyridyl)-5-pentyl resorcinol hydrochloride Olivetol (9.0 g) and N-methyl-2,6-ethylidene-4-piperidone (tropinone) (6.96 g) on 30 ml acetic acid was saturated with HCl gas. After 7 days, ether was added and the resulting solid crystallized from ethanol-ether to give 13.1 g of product, m.p. 262°–264°.

EXAMPLE XXIV 2-(N-Methyl-2,6-ethylidene-4-piperidino)-5-pentyl resorcinol hydrochloride The product of Example XXIII (5.0 g) in 2-methoxy ethanol was hydrogenated using 5% Pd on carbon as a catalyst, giving 4.50 g product, m.p. 272°–274°.

EXAMPLE XXV 2-(N-Methyl-2,6-ethylidene-1,2,3,6-tetrahydro-4-pyridyl)-5-(1,2-dimethylheptyl) resorcinol hydrochloride 1,2-Dimethylheptyl resorcinol (11.82 g) and tropinone (6.96 g) were reacted as described in Example XX to give 13.1 g of product, m.p. 178°–180°.

EXAMPLE XXVI 2-(N-Methyl-1,2,3,6-tetrahydro-4-pyridyl)-3-methoxy-5-(1,2-dimethylheptyl)phenol hydrochloride 5-(1,2-Dimethylheptyl)-3-methoxyphenol (10.0 g) of Example V, and N-methyl-4-piperidone (4.45 g) were dissolved in 20 ml acetic acid and saturated with HCl gas. Ether was added and the resulting solid recrystallized from isopropyl alcohol-ether. Yield 7.32 g, m.p. 96°–97°.

EXAMPLE XXVII 2-(N-Benzyl-1,2,3,6-tetrahydro-4-pyridyl)-3-methoxy-5-(1,2-dimethylheptyl)phenol hydrochloride 5-(1,2-Dimethylheptyl)-3-methoxyphenol (11.0 g) and N-benzyl-4-piperidone (8.35 g) were reacted as described in Example XXVI to give 13.0 g of product, m.p. 235°–237° (68% yield).

EXAMPLE XXVIII 2-(1,2,3,4-Tetrahydro-4-pyridyl)-3-methoxy-5-(1,2-dimethylheptyl)phenol hydrochloride The compound of Example XXVII (8.0 g) in 2-methoxyethanol was hydrogenated using 5% Pd on carbon as a catalyst and stopping the reaction after one equivalent was taken up. The product (5.3 g) had an m.p. of 192°–194° (83%).

EXAMPLE XXIX 2-(N-Propargyl-1,2,3,4-tetrahydro-4-pyridyl)-3-methoxy-5-(1,2-dimethylheptyl)phenol The compound of Example XXXI was dissolved in chloroform and neutralized by shaking with potassium carbonate in water. The chloroform layer was dried ($Na_2SO_4$) and the solvent removed in vacuum. The residue was dissolved in 50 ml dimethyl formamide and 1.82 g propargyl bromide was added after 20 hours at room temperature. 100 ml water was added. The resulting solid was crystallized from ether-hexane to give 1.82 g (37% yield) m.p. 113°–115°.

EXAMPLE XXX 2-(4-Piperidino)-3-methoxy-5-(1,2-dimethylheptyl)-phenol hydrochloride The compound of Example XXVII (4.57 g) was hydrogenated by the method of Example XVI giving 3.40 g (92%) yield of product, m.p. 234°–236°.

EXAMPLE XXXI

Antisecretory Activity of Piperidino Resorcinols and Related Compounds in the Pylorous Ligated Rat Model To determine the antisecretory activity of the present compounds, the compounds were tested for such activity in pylorous ligated rats. In this test, male Sprague-Dawley rats weighing 170–190 g. were fasted for 24 hours. Water was allowed ad libitum. All groups were comprised of six rats. Thirty minutes prior to ligation, the test compound was administered at an oral dose of 50 mg./kg. Water was withheld after drug administration. Ligation of the pyrloric sphincter was performed under ether anesthesia, and four hours after ligation the animals were sacrificed with $CO_2$. The stomach was dissected out and the contents were expelled into a graduated centrifuge tube. The samples were centrifuged and the volume, less debris, was measured. Sample aliquots were titrated with 0.05 N NaOH to determine acid concentration. Pepsin activity was determined on an auto analyzer using hemoglobin as the substrate by the method of Anson. Group means for volume, acid and pepsin concentrations, and pepsin outputs were compared for statistically significant differences from control means by Student's t-test. The results are recorded, below, in Table 1.

TABLE 1

ANTISECRETORY ACTIVITY OF PIPERIDINO RESORCINOLS AND RELATED COMPOUNDS IN THE PYLORUS LIGATED RAT MODEL

| Compound of Example | Oral Dose (mg./kg.) | PERCENT INHIBITION[d] OF | | | | |
|---|---|---|---|---|---|---|
| | | Volume | Acidity | Acid Output | Pepsin | Pepsin Output |
| XII | 50 | 15.5[a] | 1.4 | 16.6[a] | −3.9 | 12.8 |
| VII | 50 | 9.5 | 7.1[a] | 15.8 | −24.6[c] | −9.9 |
| XI | 50 | 63.8[c] | 22.8[a] | 68.2[c] | −36.0[b] | 47.1[b] |
| VI | 100 | 67.5[c] | 62.1[c] | 87.7[c] | −48.8[a] | 53.3[c] |
| | 50 | 67.3[c] | 51.7[c] | 84.4[c] | −38.6[c] | 54.7[c] |
| | 25 | 66.1[c] | 49.9[c] | 80.9[c] | −22.3[a] | 60.2[c] |
| | 12.5 | 49.8[c] | 21.6[c] | 59.4[c] | −25.3 | 41.2[b] |
| | 6.3 | 18.9[a] | 7.0 | 23.4[a] | −13.6 | 7.0 |
| VIII | 50 | 57.4[c] | 41.5[c] | 74.4[c] | −2.0 | 55.9[c] |
| XIII | 50 | 32.0[b] | 9.7 | 37.9[b] | 7.1 | 36.4[c] |
| IX | 50 | 21.9[c] | 12.1[c] | 31.7[c] | −7.2 | 17.0[a] |
| XIX | 50 | 25.5 | 4.2 | 27.3 | 6.9 | 31.7[a] |
| X | 100 | 1.7 | 68.4[c] | 69.0[b] | 63.0[c] | 63.2[b] |
| | 50 | 7.7 | 66.8[c] | 69.3[c] | 41.5[b] | 48.0[b] |
| | 25 | 1.4 | 20.9[a] | 22.9 | 45.1[c] | 46.4[a] |
| | 12.5 | −2.8 | 13.1[a] | 10.8 | 23.4[a] | 22.6 |
| XX | 100 | 44.8[a] | 19.5 | 51.2[a] | — | — |
| | 50 | 42.8[b] | 10.7[a] | 47.8[a] | — | — |
| | 25 | 16.9 | 1.7 | 17.1 | — | — |
| | 12.5 | 2.6 | 8.5 | 9.7 | — | — |
| XV | 100 | 12.9 | 43.6[c] | 52.8[b] | 34.5[a] | 41.4 |

TABLE 1-continued
ANTISECRETORY ACTIVITY OF PIPERIDINO RESORCINOLS AND RELATED COMPOUNDS IN THE PYLORUS LIGATED RAT MODEL

| Compound of Example | Oral Dose (mg./kg.) | Volume | Acidity | Acid Output | Pepsin | Pepsin Output |
|---|---|---|---|---|---|---|
| | 50 | −1.4 | 24.3[b] | 22.8 | 53.8[c] | 54.3[b] |
| XIV | 100 | 72.1[c] | 31.6[a] | 79.7[c] | — | — |
| | 50 | 48.9[b] | 24.7[a] | 57.6[b] | 12.7 | 52.4[b] |
| | 25 | 4.9 | 9.2 | 12.5 | — | — |
| | 12.5 | −5.9 | −0.5 | −17.3 | — | — |
| XXVI | 50 | −0.3 | 53.1[c] | 53.7[b] | 12.6 | 8.6 |
| XXVIII | 100 | −23.1[a] | 71.7[c] | 64.4[c] | 20.9 | 1.8 |
| | 50 | 3.7 | 67.1[c] | 68.2[c] | 7.5 | 9.1 |
| | 25 | −19.5[a] | 27.2[c] | 13.1 | 17.2 | 0.8 |
| | 12.5 | −14.5[a] | 19.2[a] | 7.5 | 22.5[a] | 10.9 |
| XXVII | 50 | −20.2 | −5.6 | −27.8 | 12.1 | −8.6 |
| XXIX | 100 | −21.8[a] | 58.1[c] | 49.5[b] | — | — |
| | 50 | −5.7 | 50.6[b] | 45.6[b] | 21.0[a] | 23.9[a] |
| | 25 | −13.0 | 18.6 | 7.8 | — | — |
| XVIII | 50 | −5.2 | 8.2 | 4.5 | 5.6 | 1.4 |
| XXI | 100 | 61.8[c] | 16.1[a] | 66.6[c] | −12.7 | 60.6[b] |
| | 50 | 58.2[c] | 15.0[a] | 64.1[c] | −6.2 | 56.4[b] |
| | 25 | 31.2[a] | 5.8 | 32.7[a] | 11.4 | 41.4[a] |
| | 12.5 | 6.5 | −4.0 | 0.5 | 11.4 | 19.9 |
| XVII | 50 | 0.3 | 38.1[b] | 38.5[a] | 40.5[c] | 40.6[b] |
| XXII | 50 | 37.3[a] | 8.5 | 37.6 | −7.1 | 30.9 |
| XVI | 50 | −8.6 | 50.7[c] | 46.6[a] | 45.1[c] | 40.3[b] |
| XXX | 50 | −8.9 | 39.9[c] | 34.7[a] | — | — |
| XXXI | 50 | −21.0[a] | 49.6[c] | 37.2[a] | 71.2[c] | 65.5[c] |
| XXXIV | 50 | −6.8 | 41.5[c] | 37.5[a] | 33.4[c] | 29.5[b] |
| XXIII | — | not tested | | | | |
| XXV | 50 | 9.7 | 21.2[a] | 29.4[a] | 1.0 | 11.0 |
| XXIV | 50 | 2.8 | −2.5 | 0.9 | 21.0[a] | 22.2[b] |

[a] t-test p<0.05
[b] p<0.01
[c] p<0.001
[d] a negative sign means stimulated rather than inhibited

EXAMPLE XXXII

In addition to the test described in Example XXXVI, some of the present compounds were tested in dogs.

In this test, female beagle dogs weighing 5.5–7.5 kg. were surgically provided with gastric fistulas at the ventral wall of the stomach near the greater curvature and just proximal to the antrum. The animals were allowed to recover for three to four weeks before handling and training were begun, and experiments were started six to eight weeks after surgery. The individually housed dogs were fasted for 20–24 hours before use. Water was allowed ad lib. Treatment selection was determined by a randomized schedule which included control groups given vehicle (0.5% Methocel ® solution) only. During the test period each dog was secured in a standing position with one collar around the neck and another around the lower abdomen. Before drug administration, the cannula plug of the gastric fistula was removed and the pH of the gastric juice was checked. Animals with acidic gastric juice (pH 4.0 or less) were replaced with alternate dogs. Then the drug was administered intragastrically (i.e.) through a special gastric cannula instillation plug, 30 minutes prior to subcutaneous administration of a gastric stimulant (pentagastrin, 10 μg/kg).

For each dog, collection of gastric juice was begun immediately after administration of the gastric stimulant and continued for two hours. The volumes of collected gastric juices were measured. The acid concentration and pepsin activity were determined for all samples by automated procedures. For the dog data, as recorded in Table 2, below, group means for volume (ml), acid concentration (acidity, mEq/l), pepsin concentration (mg/ml), acid output (mEq/2 hr), and pepsin output (mg/2 hr) were compared with the respective control means using Student's t-test. The results were also expressed as percent inhibition of the respective individual mean control values.

Group means for volume, acid and pepsin concentrations, acid and pepsin outputs were compared for statistically significant differences from control means by Student's t-test.

TABLE 2
ANTISECRETORY ACTIVITY OF SELECTED COMPOUNDS IN THE PENTAGASTRIN STIMULATED FISTULA DOG

| Example No. | Dose[d] | Volume | Acidity | % Inhibition Acid Output | Pepsin | Pepsin Output |
|---|---|---|---|---|---|---|
| XVI | 10 | −0.2 | 20.9 | 20.3 | 39.7 | 39.1 |
| XIV | 10 | −12.3 | 1.2 | −10.4 | −10.0 | −23.1 |
| XXVIII | 10 | 9.2 | 7.7 | 16.5 | 29.7[a] | 35.1[a] |
| | 20 | −12.6 | 26.2[c] | 17.9 | 48.0[c] | 41.2[c] |

TABLE 2-continued
ANTISECRETORY ACTIVITY OF SELECTED COMPOUNDS IN THE PENTAGASTRIN STIMULATED FISTULA DOG

| Example No. | Dose[d] | Volume | Acidity | % Inhibition Acid Output | Pepsin | Pepsin Output |
|---|---|---|---|---|---|---|
| VI | 20 | −17.6 | 36.6[a] | 26.6 | 62.7[b] | 57.1[a] |

[a] t-test $p<0.05$
[b] $<p\ 0.01$
[c] $<p\ 0.001$
[d] Oral dose mg./kg.

Among the pharmaceutically acceptable acid addition salts useful in conjunction with the present compounds, the following are the most common ones producing the desired antisecretory results: hydrochloric, sulfuric, phosphoric, citric, succinic, and acidic acids. Of course, those skilled in the art will readily be able to determine other usable acids to make pharmaceutically acceptable salts of the claimed compounds.

I claim:

1. A compound of the formula

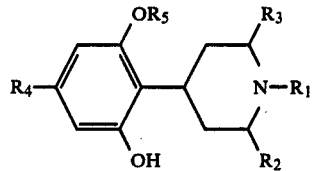

wherein $R_1$ is phenethyl; each of $R_2$, $R_3$ and $R_5$ is H; $R_4$ is n-pentyl.

* * * * *